United States Patent [19]

Harkrader et al.

[11] Patent Number: 5,066,483
[45] Date of Patent: Nov. 19, 1991

[54] ORAL RINSE COMPOSITIONS

[75] Inventors: Ronald J. Harkrader; Richard R. Jones; Kenneth S. Peterson, all of Fort Collins, Colo.

[73] Assignee: Vipont Pharmaceutical, Inc., Fort Collins, Colo.

[21] Appl. No.: 583,835

[22] Filed: Sep. 17, 1990

Related U.S. Application Data

[62] Division of Ser. No. 322,659, Mar. 13, 1989, abandoned.

[51] Int. Cl.$^5$ .................... A61K 7/22; A61K 35/78
[52] U.S. Cl. ..................... 424/54; 424/195.1
[58] Field of Search .................... 424/49, 54, 195.1

[56] References Cited

U.S. PATENT DOCUMENTS

| | | | |
|---|---|---|---|
| 4,011,309 | 3/1977 | Lutz | 424/49 |
| 4,145,412 | 3/1979 | Cadanyl | 424/58 |
| 4,146,607 | 3/1979 | Ritchey | 424/642 |
| 4,152,418 | 5/1979 | Pader | 424/50 |
| 4,339,432 | 6/1982 | Ritchey et al. | 424/49 |
| 4,376,115 | 3/1983 | McCrorey | 424/642 |
| 4,406,881 | 9/1983 | Ladanyl | 424/49 |
| 4,416,867 | 11/1983 | Ritchey et al. | 424/49 |
| 4,425,325 | 1/1984 | Ritchey et al. | 424/49 |
| 4,517,172 | 5/1985 | Southard | 424/49 |
| 4,545,979 | 10/1985 | Ambike et al. | 424/52 |
| 4,550,018 | 10/1985 | Ambike et al. | 424/52 |
| 4,562,063 | 12/1985 | Hayes et al. | 424/49 |
| 4,562,065 | 12/1985 | Hayes et al. | 424/49 |
| 4,562,066 | 12/1988 | Hayes et al. | 424/49 |
| 4,568,540 | 2/1986 | Asano et al. | 424/52 |
| 4,590,061 | 5/1986 | Southard | 424/58 |
| 4,647,452 | 3/1987 | Ritchey et al. | 424/642 |
| 4,683,133 | 7/1987 | Southard | 424/49 |
| 4,767,861 | 8/1988 | Boulware | 424/195.1 |
| 4,769,452 | 9/1988 | Boulware | 424/195.1 |
| 4,818,533 | 4/1989 | Boulware et al. | 424/195.1 |
| 4,895,727 | 1/1990 | Allen | 424/642 |
| 4,911,927 | 3/1990 | Hill et al. | 424/443 |
| 4,961,923 | 10/1990 | Heyde | 424/54 |
| 4,978,684 | 12/1990 | Cerami et al. | 424/54 |

Primary Examiner—Shep K. Rose
Attorney, Agent, or Firm—Dean P. Edmundson

[57] ABSTRACT

Mouthrinses containing sanguinarine of superior efficacy and increased uptake into dental plaque are attained by the development of stable mouthrinses adjusted to a pH in the range of 4.0 to 5.6, preferably about 4.5. The compositions may contain a zinc salt as an optional ingredient. Various types of buffer systems are described.

10 Claims, No Drawings

ORAL RINSE COMPOSITIONS

This is a divisional of co-pending application Ser. No. 07/322,659 filed on Mar. 13, 1989, now abandoned.

FIELD OF THE INVENTION

This invention relates to novel sanguinarine mouthrinses stabilized at a pH which provides improved uptake of sanguinaria into plaque and improved protection against acid production by salivary bacteria after a glucose challenge.

BACKGROUND OF THE INVENTION

Sanguinarine canadensis is known as Bloodroot, Puccoon, Tetterwort, etc. and is an herb native to North America. The plant and its juices have been used for various purposes during pre-history as well as written history. It has been used as a natural historic folk remedy medicine. The plant has been generally used whole either undried (fresh) or dried. The usual procedure is to powder the dried plant and mix it with a carrier. This folk remedy has been tried for such things as asthma, bronchitis, dysentery, ringworm, and a substantial list of other ailments.

Sanguinarine, chelerythrine, and other benzophenanthridine alkaloids are known alkaloids defined as isoquinolines. Plant sources for these alkaloids fall into various species; the Papaveraceae, Fumariaceae, and Rutaceae families. Recoveries of these alkaloids from *Sanguinaria Canadensis L.* and *Macleaya species* are described in U.S. Pat. Nos. 4,145,412; 4,406,881; 4,517,172; 4,590,061; 4,599,228; 4,683,133; 4,689,216; 4,767,861; and 4,769,452. Production of these alkaloids from plant tissue culture has been described in *Plant Cell Reports* (1988) 7:410-413.

Purification of the Benzophenanthridine alkaloids into individual alkaloids without using known chromatographic methods is also described in the foregoing U.S. patents.

The use of an extract containing these benzophenanthridine alkaloids from Sanguinaria Canadensis as an ingredient in an oral cleansing preparation is also disclosed in the foregoing U.S. patents.

Other uses for the extract of Sanguinaria Canadensis L. are reported as a plaque disclosing agent in U.S. Pat. Nos. 4,517,172 and 4,590,061.

It is known that mouthrinses and dentifrices containing sanguinaria extract are effective anti-plaque and anti-gingivitis agents. They are also effective against oral malodor and calculus. Early patents, U.S. Pat. Nos. 209,331 and 2,344,830 describe the use of sanguinaria in combination with zinc chloride. Although there is no indication that zinc chloride is needed to maintain efficacy, sanguinaria extract is typically used in combination with zinc chloride or other metallic salts, such as stannous chloride, in dentifrices, as in U.S. Pat. No. 4,689,216. When sanguinaria extract is combined with zinc chloride in a mouthrinse vehicle the pH is usually adjusted to 3. Prior art teaches that zinc mouthrinses are adjusted to pH 3 to prevent the formation of insoluble zinc compounds such as zinc hydroxide and zinc oxychloride. See U.S. Pat. No. 4,289,755. In addition, solutions of sanguinaria are acidified to prevent the formation of pseudo base forms of the benzophenanthridine alkaloids present in the extract. Pseudo base forms of the alkaloids present in the extract begin to form at approximately pH 5.6 (Jones, et al. J. of Natural Products, Vol 49, No. 6, pp. 1109-1111, November-December 1986).

In addition, the extract was adjusted to a pH of 3 to maintain chemical stability of the extract and prevent the formation of brownish to black precipitates which are assumed to be due to the condensation of tannins and to the presence of lignin-like material in the extract. It has been found that 1% solutions of sanguinaria extract filtered at pH's of 3, 4, and 5 will form additional precipitates on standing with the minimum amount of precipitate forming at pH 3. This indicates that at pH's above 3 undesirable condensation and/or polymerization begins to occur.

The alkaloid extract when made into an oral rinse, dentifrice, or oral care product is an excellent breath freshener, and also an anti-plaque and anti-gingivitis agent. When combined with zinc chloride, however, the pH of the rinse needs to be acidic (pH=3) for a number of reasons. Zinc containing rinses are generally formulated at a pH of 3 for stability purposes as set forth in U.S. Pat. No. 4,289,755. Other patent art teaches that higher pH's are attainable through the use of glycine. See U.S. Pat. No. 4,339,432. Rinses at low pH's, especially with zinc chloride, also taste acrid.

SUMMARY OF THE INVENTION

In accordance with the present invention, novel mouthrinses containing sanguinaria extract of superior stability and improved uptake of sanguinaria into plaque, and improved protection against acid production by salivary bacteria, are attained by adjusting the pH of the rinses to 4.0 to 5.6, preferably 4.5, using selective buffer systems and by using emulsifiers with improved chemical compatibility with the extract. It was also discovered that impurities in emulsifiers can be detrimental to the stability of the extract. It was also shown that rinses at pH 4.5 can be used to significantly reduce malodor for a period of 8 hours when compared to a placebo rinse.

DETAILED DESCRIPTION OF THE INVENTION

The oral rinse compositions of this invention are aqueous based. The compositions include one or more benzophenanthridine alkaloids* and may also contain one or more zinc salts, if desired, such as zinc chloride.

*The benzophenanthridine alkaloids which are useful in the composition of this invention include sanguinarine, chelerythrine, sanguilutine, chelilutine, chelirubine, and sanguirubine.

It has now been found that the formation of precipitates in oral compositions containing benzophenanthridine alkaloids and zinc salts can be prevented by the use of a buffer system. A stable pH and precipitation-free composition which may contain zinc salts is provided.

Other useful zinc salts which may be included are, for example, zinc acetate, zinc gluconate, zinc sulfate, zinc salicylate, zinc tartrate, zinc lactate, zinc phenolsulfonate, and zinc carboxymethyloxysuccinate. Preferably the zinc salt is soluble in water in the amount present in the composition, although salts which are not water-soluble may also be used if they are properly suspended or emulsified. For example, see the zinc salts described in U.S. Pat. No. 4,100,269.

The amount of zinc salt present may vary up to about 0.5% by weight. Preferably, if a zinc salt is used it is present in an amount of about 0.05 to 0.25% by weight.

The oral rinse compositions of this invention generally include, in addition to the benzophenanthridine alkaloid, about 50 to 95% by weight water (Preferably about 75 to 90%); 5 to 25% by weight ethyl alcohol (preferably about 5 to 15%); 2 to 15% by weight of glycerine or other suitable humectant; 0.1 to 3.0% surface active agent (i.e. emulsifier); 0.02 to 1.0% by weight sweetening agent; 0.05 to 0.4% by weight flavoring agents; and 0 to 0.01 % by weight coloring agents.

Other humectants suitable for this application include sorbitol, mannitol, propylene glycol, and polyethylene glycols used individually or as combinations thereof. The function of these humectants are as texture, body, and flavor modifiers and as solubilizers.

The type of surface active agents suitable for this application include:

Anionics, such as sodium lauryl sulfates, sodium lauryl succinates, and sodium dodecylsulfonates.

Nonionics such as Polyoxyethylene sorbitan fatty acid esters, e.g. PEG (20) sorbitan isosterate, Polysorbate 20, Polysorbate 60, Polysorbate 80 and amine oxides, e.g. cocoamine oxide.

Amphoteric such as cocoamphocaboxypropionate and alkylbetaines e.g. cocoamido betainses.

These surfaces active agents are used individually or in combinations there of.

The type of sweetening agents suitable for this application include, aspartame, acesulfame K, xylitol, sodium cyclamate, saccharin, and some humectants such as sorbitol, and mannitol. Flavoring agents used in the compositions of this invention should be free of sulfur compounds present in small amounts in natural mint oils such as pulegone, sabadine, and mercaptans.

The buffer system which is included in the oral rinse composition of the invention is capable of maintaining the pH of the compositions in the desired range of about 4.0 to 5.6. In this pH range the stability of the compositions is very good, precipitates are avoided, and good uptake of alkaloid into plaque is attained.

There are a number of buffer systems which are useful in the compositions of the invention. When no zinc salts are present in the composition the following buffer systems are useful herein:
Sodium Citrate/Citric Acid
Sodium Acetate/Acetic Acid
Sodium Tartrate/Tartaric Acid
Sodium Phosphate/Phosphoric Acid
Sodium Succinate/Succinic Acid
Sodium Lactate/Lactic Acid
Sodium Propionate/Propionic Acid When zinc salts are present in the composition, the useful buffer systems are as follows:
Sodium Citrate/Citric Acid
Sodium Acetate/Acetic Acid
Sodium Tartrate/Tartaric Acid The invention is further illustrated by means of the following examples.

EXAMPLE I

An oral rinse composition was prepared using the ingredients listed below in the amounts stated.

| Part | Ingredients | % by Weight |
|---|---|---|
| A | Purified Water | 80.25 |
|  | ZnCl$_2$ | 0.20 |
|  | Glycerin | 3.00 |

-continued

| Part | Ingredients | % by Weight |
|---|---|---|
|  | Sodium Saccharin | 0.076 |
| B | Ethyl-Alcohol 190 Proof | 10.00 |
|  | Poloxamer 237 | 0.20 |
|  | Polysorbate 80 | 0.20 |
|  | Flavor | 0.20 |
| C | Buffer system: | |
|  | Tri Sodium Citrate.2H$_2$O | 0.28 |
|  | Citric Acid Anhydrous | 0.016 |
| D | Fluid Extract (Sanguinaria) 1% Aqueous Solution | 3.00 |
| E | Purified Water | 2.578 |
|  |  | 100.00% | pH 4.48, 4.49

It is important to note that to achieve optimum stability of the rinse composition, the buffer system (part C) must be added to the rinse base (parts A and B) prior to the addition of the sanguinaria extract (part D) in order to avoid color changes and formation of precipitates.

Examples of other specific buffer systems which are useful in the compositions of this invention are illustrated in the following examples II and III.

EXAMPLE II

| Part | Ingredient | % W/W |
|---|---|---|
| A | Purified Water | 80.25 |
|  | Zinc Chloride | 0.20 |
|  | Glycerin | 3.00 |
|  | Sodium Saccharin | 0.076 |
| B | Ethyl Alcohol 190 Proof | 10.00 |
|  | Poloxamer 237[1] | 0.20 |
|  | Polysorbate 80[2] | 0.20 |
|  | Flavor Oil | 0.20 |
| C | Sodium Acetate | 1.09 |
|  | Acetic Acid, Glacial | 0.10 |
| D | Sanguinaria Extract Solution, 1% | 3.00 |
| E | Purified Water | 1.684 |
|  |  | 100.00% |

EXAMPLE III

| Part | Ingredient | % W/W |
|---|---|---|
| A | Purified Water | 80.25 |
|  | Zinc Chloride | 0.20 |
|  | Glycerin | 3.00 |
|  | Sodium Saccharin | 0.076 |
| B | Ethyl Alcohol 190 Proof | 10.00 |
|  | Poloxamer 237[1] | 0.20 |
|  | Polysorbate 80[2] | 0.20 |
|  | Flavor oil | 0.20 |
| C | Sodium Tartrate | 0.60 |
|  | Tartaric Acid | 0.02 |
| D | Sanguinaria Extract Solution, 1% | 3.00 |
| E | Purified Water | 2.254 |
|  |  | 100.00% |

[1]Pluronic F-87, commercially available from BASF-Wyandotte is a polyoxyethylene, polyoxypropylene block polymer.
[2]Tween 80, commercially available from ICI Americas is a mixture of oleate esters of sorbitol and sorbitol anhydrides consisting of predominantly of monoesters, condensed with approximately 20 moles of ethylene oxide.

The oral rinses listed above are prepared in the following manner.

Part A ingredients are added to main mix vessel in order listed, allow 5 minute mix in between each addition and a 15 minute mix when all of Part A is added.

Part B ingredients are added to a separate mix vessel in order listed, allow 5 minute mix in between each addition and a 15 minute mix when all of Part B is added.

Part B is added to Part A in the main mix vessel and mixed for 15 minutes.

Part C is dry blended and added to the main mix vessel and mixed for 15 minutes. It is important to note that to achieve optimum stability of the rinse the buffers, "Part C", must be added to the rinse base prior to the addition of the Sanguinaria Extract Solution, Part D. Color changes and precipitates may occur if this process is not followed.

Part D is added to the main mix vessel, followed by Part E which is used to rinse Part D vessel.

After the addition of Part E mix entire formula for 30 minutes and then pass through a filter having nominal pore size of 0.5 microns.

Another example of an oral rinse composition containing sanguinaria and zinc salt is as follows:

EXAMPLE IV

| Part | Ingredient | % W/W |
|---|---|---|
| A | Purified Water | 80.25 |
|   | Zinc Chloride | 0.20 |
|   | Sorbitol, 70 | 4.11 |
|   | Sodium Saccharin | 0.076 |
| B | Ethyl Alcohol 190 Proof | 10.00 |
|   | Poloxamer 237[1] | 0.20 |
|   | Polysorbate 80[2] | 0.20 |
|   | Flavor Oil | 0.20 |
| C | Tri Sodium Citrate.2H$_2$O | 0.28 |
|   | Citric Acid Anhydrous | 0.016 |
| D | Sanguinaria Extract Solution, 1% | 3.00 |
| E | Purified Water | 1.468 |
|   |  | 100.00% |

In order to maintain a stable pH and a precipitation free rinse containing Sanguinaria in the absence of zinc, the formulation and buffer system is not limited to previously mentioned examples.

Listed below is an additional formulation example in which there are no zinc salts present.

EXAMPLE V

| Part | Ingredient | % W/W |
|---|---|---|
| A | Purified Water | 80.25 |
|   | Glycerin | 3.00 |
|   | Sodium Saccharin | 0.076 |
| B | Ethyl Alcohol 190 Proof | 10.00 |
|   | Poloxamer 237[1] | 0.20 |
|   | Polysorbate 80[2] | 0.20 |
|   | Flavor Oil | 0.20 |
| C | Tri Sodium Citrate.2H$_2$O | 0.10 |
|   | Citric Acid Anhydrous | 0.07 |
| D | Sanguinaria Extract Solution, 1% | 3.00 |
| E | Purified Water | 2.904 |
|   |  | 100.00% |

Other buffer system examples which can be substituted for the citrate buffers in Part C are as follows:
Tartrate buffers
Acetate buffers
Phosphate buffers
Succinate buffers
Lactate buffers
Propionate buffers The oral rinses listed above are prepared using the same procedure previously discussed.

It has also been found that sanguinaria extract becomes more chemically active as the pH is adjusted above three and can react with impurities that are present in some excipients used in the mouthrinse. For example a mouthrinse composition that shows good chemical stability at a pH of 3.0 shows significant loss in sanguinarine content when the mouthrinse is adjusted to pH 4.5 to pH 5.5. As can be shown in the following example:

EXAMPLE VI

| | | Stability of Sanguinaria in Rinses | |
|---|---|---|---|
| Wt. % Poloxamer 407 | pH | Initial SaCl,* ppm | Aged 3 Months at 40° C. SaCl,ppm |
| 0.1 | 2.7 | 100 | 73 |
| 0.1 | 4.5 | 99 | 58 |
| 0.1 | 5.0 | 109 | 33 |

*Sanguinarine chloride

In determining the reason for the loss of sanguinaria stability at elevated pH's it was unexpectedly found that this decreased stability at the elevated pH's was in part due to a surfactant (poloxamer 407). This nonionic surfactant is a block copolymer of polyoxyethylene and polyoxypropylene. The following data on mouthrinses formulated at pH 6.0 shows that as the concentration of poloxamer is increased in a mouthrinse the stability of sanguinaria decreases.

| Wt. % Poloxamer 407 | 3 Day Stability 40° C. SaCl, ppm |
|---|---|
| 0.3 | 94 |
| 0.6 | 49 |
| 0.9 | 20 |

Poloxamer 237 shows improved stability in rinses formulated at elevated pH's as shown by the following data:

| | | | Stability at 40° C. | |
|---|---|---|---|---|
| 0.1 Wt. % Poloxamer | pH | Initial | SaCl, ppm | Age-Weeks |
| 407 | 4.5 | 101 | 45 | 10 |
| 407 | 5.0 | 106 | 40 | 10 |
| 237 | 4.5 | 92 | 77 | 13 |
| 237 | 5.2 | 95 | 71 | 13 |

It was determined that the poloxamer 407 has a higher level of unsaturation than poloxamer 237 as shown in the following table:

| Surfactant | Unsaturation Meq/mg |
|---|---|
| Poloxamer 407 | 48 |
| Poloxamer 237 | 34 |

Unsaturation was determined by reacting methanolic mercuric acetate with the poloxamer, adding sodium bromide and then titrating the liberated acetic acid with methanolic potassium hydroxide.

EXAMPLE VII

The clinical efficacy of sanguinaria extract is due in part to its antimicrobial activity. Sanguinarine is known to inhibit 98% of the organisms found in dental plaque. (*Antimicrobial Agents and Chemotherapy*, April 1985, 27:4:663-665) Its MIC is generally 16 PPM or less for these organisms. It is knwon that sanguinarine extract is absorbed into plaque and onto oral soft and hard tissues (JADA Vol 108, March 1984, p. 338). It has now been discovered that by raising the pH of the mouthrinse from 3.0 to 4.5-5.6 there is an increased uptake of sanguinarine and total benzophenanthridine alkaloids into dental plaque as shown by the following table:

| Sanguinarine and Total Benzophenanthridine Alkaloids Taken Into Wet Plaque From Mouthrinses | | | | |
|---|---|---|---|---|
| % SaCl | % ZnCl$_2$ | pH | Sanguinarine µg/g wet plaque | Total Benzophenanthridine Alkaloids µg/g plaque |
| 0.03 | 0.2 | 3.2 | 35.6 | 62.7 |
| 0.03 | — | 4.5 | 59.6 | 118.3 |
| 0.03 | 0.2 | 4.5 | 44.2 | 77.6 |
| 0.03 | — | 5.6 | 61.1 | 126.8 |
| 0.03 | 0.2 | 5.6 | 41.5 | 74.4 |

EXAMPLE VIII

In addition to measuring the uptake of sanguinaria extract into plaque, the efficacy of pH 3 and pH 4.5 rinses was measured using a modified saliva glucose test. An initial saliva sample was taken (background) and then subjects rinsed for one minute with a test rinse. The purpose of the background saliva sample was to measure shifts in the pH of the sample over time following the glucose challenge. One hour after rinsing with sanguinaria rinses with pH's adjusted to either pH 3.2 or pH 4.5 the saliva of the subjects was again collected under standard conditions. Glucose was then added to the background saliva samples and test saliva samples and the mixtures were incubated for three hours at 37° C. The pH's of these mixtures was monitored at 15, 30, 60, 120, and 300 minutes. Inhibition of salivary glycolysis was measured by subtracting the background pH reading at each timepoint from the test pH reading of the corresponding timepoint. Most of the background saliva samples rapidly decreased in pH after the addition of glucose. Thus, if the rinse treatment provides a protective effect the fall in pH is slow. The larger the difference, therefore, between the test and background pH, the better the inhibition of salivary glycolysis.

The following table shows that a treatment with a pH 4.5 rinse was more effective than treatment with a pH 3.2 rinse. The number of subjects was seven per group. The initial readings were used to adjust the outcome pH levels at each timepoint in order to test for differences between groups. The difference between the test rinses was statistically significant using analysis of covariance (ANCOVA) at a significance level of $P<0.05$.

| Inhibition of Salivary Glycolysis 5% Glucose added to Saliva Taken at Baseline and One Hour After Rinsing | | |
|---|---|---|
| Time (Minutes) | pH 4.5 Rinse ΔpH | pH 3.2 Rinse ΔpH |
| 15 | 1.595 | 1.465 |
| 30 | 1.990 | 1.626 |
| 60 | 2.148 | 1.720 |
| 120 | 2.160 | 1.523 |
| 300 | 2.093 | 1.055 |

ΔpH = Sample pH-Background pH at each time period

What is claimed is:

1. A stable oral rinse composition comprising from about 0.01 to 0.2% by weight of benzophenanthridine alkaloid in an aqueous solution and a buffer system in a quantity sufficient to adjust the pH of said composition to a pH in the range of 4.0 to 5.6.

2. A composition in accordance with claim 1, wherein said alkaloid is selected from the group consisting of water soluble salts of sanguinarine, chelerythrine, sanguilutine, chelilutine, chelirubine, and sanguirubine.

3. A composition in accordance with claim 1, wherein said buffer system is selected from the group consisting of (a) sodium citrate and citric acid, (b) sodium acetate and acetic acid, (c) sodium tartrate and tartaric acid, (d) sodium phosphate and phosphoric acid; (e) sodium succinate and succinic acid; (f) sodium lactate and lactic acid; (g) sodium propionate and propionic acid.

4. A composition in accordance with claim 1, further comprising 5 to 25% by weight ethyl alcohol, 2 to 15% by weight of humectant, 0.1 to 3% by weight surface active agent, 0.02 to 1% by weight sweetening agent, and 0.05 to 0.4% by weight flavoring agent.

5. A composition in accordance with claim 1, wherein said alkaloid is selected from the group consisting of sanguinarine and chelerythrine; and wherein said composition has a pH of about 4.5.

6. A method for stabilizing an oral rinse composition of the type comprising benzophenanthridine alkaloid in an aqueous solution, the method comprising the step of adding to said composition a buffer system in a quantity sufficient to adjust the pH of said composition into the range of 4.0 to 5.6.

7. A method in accordance with claim 6, wherein said alkaloid is selected from the group consisting of water soluble salts of sanguinarine, chelerythrine, sanguilutine, chelilutine, chelirubine, and sanguirubine.

8. A method in accordance with claim 6, wherein said buffer system is selected from the group consisting of (a) sodium citrate and citric acid, (b) sodium acetate and acetic acid, (c) sodium tartrate and tartaric acid, (d) sodium phosphate and phosphoric acid; (e) sodium succinate and succinic acid; (f) sodium lactate and lactic acid; (g) sodium propionate and propionic acid.

9. A method in accordance with claim 6, wherein said composition further comprises 5 to 25% by weight ethyl alcohol, 2 to 15% by weight of humectant, 0.1 to 3% by weight surface active agent, 0.02 to 1% by weight sweetening agent, and 0.05 to 0.4% by weight flavoring agent.

10. A method in accordance with claim 6, wherein said alkaloid is selected from the group consisting of sanguinarine and chelerythrine; and wherein the pH of said composition is adjusted to about 4.5.

* * * * *

UNITED STATES PATENT AND TRADEMARK OFFICE
CERTIFICATE OF CORRECTION

PATENT NO. : 5,066,483

DATED : November 19, 1991

INVENTOR(S) : John J. Donohue, Ronald J. Harkrader, Richard R. Jones, Kenneth S. Peterson It is certified that error appears in the above—identified patent and that said Letters Patent is hereby corrected as shown below:

On the title page:  --[75] Inventors: John J. Donohue, Ronald J. Harkrader, Richard R. Jones, Kenneth S. Peterson, all of Fort Collins, Colorado --

Signed and Sealed this

Twenty-second Day of June, 1993

Attest:

MICHAEL K. KIRK

Attesting Officer

Acting Commissioner of Patents and Trademarks